United States Patent

Weerasooriya et al.

[11] Patent Number: 6,020,509
[45] Date of Patent: Feb. 1, 2000

[54] METHOD FOR PRODUCING SURFACTANT COMPOSITIONS

[75] Inventors: Upali Weerasooriya, Austin; Paul A. Filler; Janet L. Watson, both of Leander, all of Tex.

[73] Assignee: Condea Vista Company, Houston, Tex.

[21] Appl. No.: 09/218,825

[22] Filed: Dec. 22, 1998

[51] Int. Cl.⁷ .................................................... C07C 51/00
[52] U.S. Cl. ........................................... 554/156; 554/124
[58] Field of Search .............................................. 554/156

[56] References Cited

U.S. PATENT DOCUMENTS 3,663,583  5/1972  Haynes .
5,220,046  6/1993  Leach et al. .
5,386,045  1/1995  Weerasooriya et al. .

*Primary Examiner*—Deborah Carr
*Attorney, Agent, or Firm*—Browning Bushman

[57] ABSTRACT

A process for producing a surfactant composition by partially saponifying an alkoxylated triglyceride having the formula:

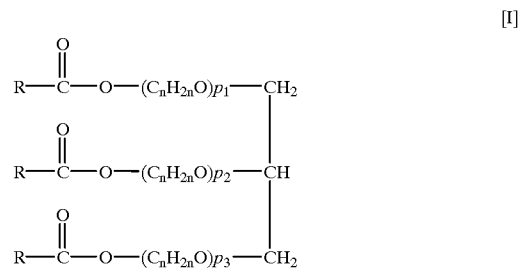

[I]

with an alkali metal hydroxide such as sodium hydroxide and recovering a surfactant composition comprising soap and moisturizing agents comprised of alkoxylated monoglycerides and unreacted alkoxylated triglycerides.

9 Claims, No Drawings

METHOD FOR PRODUCING SURFACTANT COMPOSITIONS

BACKGROUND OF THE INVENTION

1. Field of the Invention

The present invention relates to a process for preparing surfactant compositions and, more particularly, to a method for producing a surfactant composition comprising a soap and alkoxylated mono- and diglycerides as moisturizing agents.

2. Description of the Prior Art

Recently, the cosmetic industry has placed greater emphasis on natural ingredients with proven mildness. In particular, ethoxylated (alkoxylated) mono- and diglycerides are known for their mildness and have been recently demonstrated to be effective moisturizing agents. Not only do these ethoxylated glycerides appear to have excellent moisturizing and mildness characteristics, they also possess surfactant properties; e.g., they are non-ionic surfactants. Accordingly, while theoretically, they could be incorporated into a soap composition—e.g., a skin cleanser—to impart moisturizing characteristics, it would clearly be desirable to have a process wherein there was produced, in a single reaction, a skin cleanser containing both soap and the ethoxylated glycerides.

It is known that hydroxylated, ethoxylated triglycerides of fatty acids—e.g., ethoxylated castor oil—can be partially saponified to form a polyoxyethylene fatty acid alkali soap. Thus, in U.S. Pat. No. 3,663,583, there is described a process for producing a saponified ethoxylated triglyceride of ricinoleic acid. Ricinoleic acid is a hydroxy fatty acid having the structure:

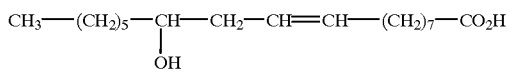

which produces a triglyceride having the following structure:

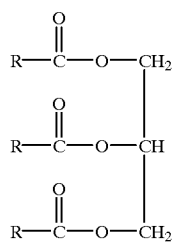

where R stands for the fatty portion of the ricinoleic acid—i.e., the portion containing the hydroxyl group and the olefinic linkage. In the process described in U.S. Pat. No. 3,663,583, conventional ethoxylation catalysts such as NaOH and KOH are used to effect the ethoxylation of the hydroxytriglyceride. As would be expected, this results in ethoxylating the hydroxy group of the castor oil such that subsequent saponification cleaves the triglyceride portion of the molecule, resulting in the formation of the polyoxyethylene ricinoleate soap. Thus, the process of U.S. Pat. No. 3,663,583 does not produce a surfactant composition that, in addition to having a soap, also contains mono- and diethoxylated glycerides to act as moisturizing agents.

It is known from U.S. Pat. No. 5,386,045 that alkoxylated triglycerides or triesters having the formula:

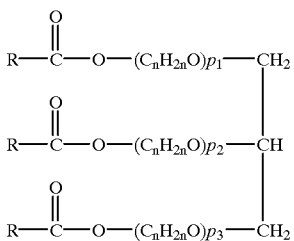

wherein n is from 2 to 4, $p_1$, $p_2$, and $p_3$ are each from about 1 to about 50, preferably 1 to 15, and R is an organic radical containing from about 6 to about 30 carbon atoms, preferably a linear or branched chain alky group, can be prepared starting by reacting an alkylene oxide, e.g., ethylene oxide, with a triglyceride having the formula:

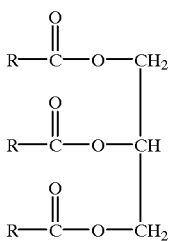

As disclosed in U.S. Pat. No. 5,386,045, the reaction is generally conducted at a temperature of from about 80° C. to about 200° C. and a pressure that can range from subambient up to about 100 psi or higher. A catalytic effective amount of a calcium catalyst is employed in the reaction. The catalyst is selected from the group consisting of (a) Calcium Catalyst A, formed by reacting a reactant mixture comprising an alkoxylated alcohol mixture containing compounds having the general formula:

$$R_1—O—(C_nH_{2n}O)_p—H$$

wherein $R_1$ is an organic radical containing from about 1 to about 30 carbon atoms, preferably a linear or branched chain all group, and p is from 1 to 50, preferably 1 to 15, a calcium-containing compound that is at least partially dispersible in said alkoxylated alcohol, an inorganic acid compound, and a metal alkoxylate of an acidic metal, the calcium-containing compound and the alkoxylated alcohol mixture being mixed prior to addition of the metal alkoxide, the reactant mixture being heated to a temperature and for a time sufficient to effect at least a partial exchange reaction between the alkoxide groups of said metal alkoxide and the hydroxyl groups of the alkoxylated alcohol; (b) Calcium Catalyst B, formed by solubilizing, at least partially, a calcium-containing compound with an activator having the formula:

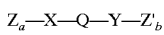

$$Z_a—X—Q—Y—Z'_b$$

wherein X and Y are the same or different electro-negative, hetero-atoms, selected from the group consisting of oxygen, nitrogen, sulfur, and phosphorus, a and b are the same or different integers satisfying the valency requirements of X and Y, Q is an organic radical that is electro-positive or essentially neutral relative to X and/or Y, and Z and Z' are the same or different and are either hydrogen or an organic radical that does not prevent said solubilizing; and (c) mixtures of Calcium Catalyst A and Calcium Catalyst B.

SUMMARY OF THE INVENTION

It is therefore an object of the present invention to provide a process for producing a surfactant composition containing a conventional soap in admixture with moisturizing agents.

Another object of the present invention is to provide a process for producing, in a single step reaction, a moisturizing skin cleanser.

The above and other objects of the present invention will become apparent from the description given herein and the appended claims.

According to the process of the present invention, an alkoxylated triglyceride of Formula I is partially saponified with an alkali metal hydroxide to produce a surfactant composition containing a soap having the formula:

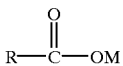

[II]

wherein M is an alkali metal, and a mixture of unreacted alkoxylated triglyceride, alkoxylated monoglyceride and alkoxylated diglyceride, the surfactant composition being recovered. One of the features of the invention is that by controlling the degree of saponification, the surfactant composition can be tailored so as to vary the ratio between the soap produced and the amount of alkoxylated mono- and/or diglycerides present in the surfactant composition.

DESCRIPTION OF THE PREFERRED EMBODIMENT

As noted above, the alkoxylated triglycerides, which are used as starting materials in the process of the present invention, are obtained from the alkoxylation of suitable triglycerides, as more fully disclosed in U.S. Pat. No. 5,386,045. Non-limiting examples of the triglycerides that can be used to form the alkoxylated triglycerides used as the starting material in the process of the present invention include triglycerides such as tributyrin, trilaurin, tristearin, etc. In general, any triglyceride of a fatty acid that does not contain a hydroxyl group in the fatty acid chain can be employed as a triglyceride starting material to form the alkoxylated triglycerides of the present invention. The triglycerides that are used to form the alkoxylated triglyceride starting materials of the present invention can be readily derived from natural sources such as whale oil; beeswax; carnauba wax; animal fat; and vegetable sources, such as palm oil, palm kernel oil, coconut oil, olive oil, cottonseed oil, soybean oil, peanut oil, etc.

The alkoxylated triglycerides of the present invention, which as noted above can be produced according to the process described above and in greater detail in U.S. Pat. No. 5,386,045 will have the general formula:

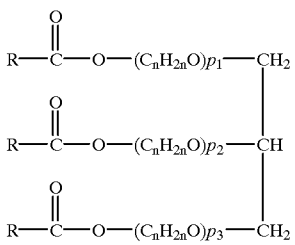

wherein n is from 2 to 4, $p_1$, $p_2$, and $p_3$ are each from about 1 to about 50, preferably 4–20, and R is an organic radical containing from about 6 to about 30 carbon atoms, and provided that the R group contains no hydroxyl groups. It is understood that the R group can contain ether linkages, ketonic structures, etc., the proviso being that the R group contain no active hydrogen atoms or other groupings that would react with the alkali metal hydroxides. Preferably, R will be a branched or straight-chain hydrocarbon radicals-i.e., an alkyl group, straight-chain or linear hydrocarbon radicals being particularly preferred. An especially desirable group of alkoxylated triglycerides are those wherein R is a branched or straight-chain hydrocarbon radical—i.e., an alkyl group having from about 6 to about 30 carbon atoms, especially from about 6 to about 20 carbon atoms.

The alkali metal hydroxide used to saponify the alkoxylated triglyceride can be sodium hydroxide, potassium hydroxide, lithium hydroxide, etc., sodium hydroxide being preferred because of its ready availability and low cost. In general, the molar ratio of alkoxylated triglyceride to alkali metal hydroxide will be greater than 0.5 and less than 3, preferably from 1:1 to 1:2.5, most preferably from 1:1 to 1:2.

As noted above, the alkoxylated triglyceride is only partially saponified with the alkali metal hydroxide; i.e., there is insufficient alkali metal hydroxide relative to the amount of alkoxylated triglyceride to cleave all of the carboxyl linkages, which would result in a high make of alkoxylated glycerol. Indeed, it is a feature of the process of the present invention that the surfactant composition produced has relatively low levels of alkoxylated glycerol and that, by varying the amount of alkali metal hydroxide relative to the amount of alkoxylated triglyceride, the surfactant composition can be tailored such that the balance between the soap portion of the composition and the mixture of ethoxylated mono- and diglycerides can be controlled; i.e., the surfactant composition can be tailored to have a higher or lower amount of the soap component and a concomitantly a lower or higher amount of the moisturizing agents.

The reaction between the alkoxylated tyriglyceride and the alkali metal hydroxide can be conducted at temperatures ranging from 25° C. to 175° C. and over a wide pressure range—e.g., from subatmospheric to 50 psi.

To more fully illustrate the invention, the following non-limiting example is presented:

EXAMPLE 1

Coconut oil that had been ethoxylated according to the process described above and more fully in U.S. Pat. No. 5,386,045, was reacted with ethylene oxide to produce an alkoxylated triglyceride containing 60% by weight ethylene oxide (60% Tricoco ETO). Although, as well known, while the chief constituent of coconut oil is the triglyceride of lauric acid, there are also appreciable amounts of the triglycerides of capric, myristic, palmitic, and oleic acids. The thus ethoxylated coconut oil was reacted with two saponification (molar) equivalents of sodium hydroxide. The experimental procedure was as follows:

A three-neck 500 ml round bottom flask was equipped with mechanical stirring.

The stir shaft was sealed using a vacuum adapter. A Pasteur pipet was inserted through a rubber stopcock and placed in one neck. The pipet end was then connected via tubing to a nitrogen supply. The flask assembly was then placed into an oil bath that was heat controlled by a Therm-O-Watch® controller. The Therm-O-Watch® controller read a thermometer that was placed into the oil bath. The Therm-O-Watch® then powered a piece of coiled resistance wire immersed in the oil bath.

Into the flask was placed 150 g of ethoxylated triglyceride. The ethoxylate was heated to 95° C. with stirring. A glass syringe was used to add a calculated amount of 50% NaOH.

The base (50% NaOH) stock solution should be standardized before use. The base should be added dropwise until the calculated addition amount is added The ethoxylated triglyceride/NaOH mixture should be stirred at 95° C. with a steady $N_2$ flow. After about 10 minutes, the temperature should be increased to 115° C. The sample mixture needs to be watched closely to prevent foaming. The water in the NaOH can cause some initial foaming of the reaction mix until a sufficient amount of water is lost. After holding at 115° C. for another 10 minutes, the sample should be heated to 160° C. and held there until the sample is saponified to the level of base added. As the sample is saponified, it should start to thicken and convert to a milky yellowish color. After an hour, a few drops of water should be carefully added, which prevents the sample from forming alkoxide. The addition of small amounts of water will destroy the alkoxide and convert it back to NaOH. This will allow the reaction to go to completion faster and keep it from darkening. After a couple of hours, a sample should be taken and titrated to determine the degree of saponification. After the sample has been saponified to the desired level, the sample is quenched with its corresponding fatty acid to lower the pH and consume any trace amounts of base left.

All the tritrations were performed potentiometrically with a Metrohm 670 titroprocessor equipped with a Brinkman combination pH electrode. All samples were titrated using standardized 0.1M HCL. One gram of partially saponified triglyceride ethoxylate was added to a 150 ml beaker. After the weight of the test sample was recorded, 50 ml of isopropyl alcohol/water was added along with a stirbar. If the test sample is not completely saponified, the sample will saponify to completion in the isopropyl alcohol/water (if it is allowed to sit for several hours). It is therefore very important to get the test sample dissolved and titrated as soon as possible.

The results are shown in Table 1 below.

EXAMPLE 2

The procedure of Example 1 was followed with the exception that the ethoxylated coconut oil contained 70% by weight ethylene oxide (70% Tricoco ETO), which was reacted with 1.9 saponification equivalents of sodium hydroxide. The results are shown in Table 1 below.

EXAMPLE 3

The procedure of Example 1 was followed, with the exception that the alkoxylated ester employed was derived from tallow oil, which, as well known, has as its main constituent the triglycerides of stearic acid, palmitic acid, and oleic acid. The ethoxylated tallow oil containing 60% by weight ethylene oxide (60% Tritallow ETO) was reacted with 1.9 saponification equivalents of sodium hydroxide. The results are shown in Table 1 below.

In Table 1 below, there is shown the amount of soap produced relative to the amount of polyethoxylated glycerol (PEG) produced, as well as a comparison of the calculated amount of polyethoxylated glycerol that would be produced assuming no ethoxylated mono- and diglyceride were present.

TABLE 1

| | "PEG" Wt. % | | |
| --- | --- | --- | --- |
| Sample | Actual | Calculated based on no mono- and diglyceride ETO | Soap Wt. % |
| 60% Tricoco ETO | 19.6 | 41.6 | 27 |
| 70% Tricoco ETO | 15.1 | 44.7 | 19 |
| 60% Tritallow ETO | 22.9 | 39.9 | 26 |

As can be seen from Table 1, the actual amount of polyethoxylated glycerol actually produced is markedly less than what would be assumed to be present (the calculated amount) on the basis that the first fatty acid group is cleaved off, the sodium hydroxide preferentially complexes to the resultant free hydroxy group, thereby cleaving off the second fatty acid group, followed by the sodium hydroxide, then complexing to the two free hydroxyl groups and cleaving off the remaining fatty acid group from the same molecule. Thus, and surprisingly, the actual amount of polyethoxylated glycerol is low, meaning that the surfactant composition contains unreacted ethoxylated triglyceride starting material plus significant amounts of ethoxylated mono- and diglycerides.

The method for determining PEG content utilizes reverse phase high performance liquid chromatography (HPLC) and size exclusion chromatography (SEC) to analyze and quantify PEG in glyceride ethoxylates. The reverse phase BPLC component of the method consists of two columns (one $C_8$ and one $C_{18}$ column) that separate PEG and other hydrophilic matrix components from glyceride ethoxylates. After hydrophilic components exit from the reverse phase columns and enter the SEC column, the direction of flow is switched on the reverse phase columns, and the strongly retained glyceride ethoxylates are eluted. In the SEC column, PEG is separated from smaller hydrophilic matrix components such as water and salts that interfere with PEG when analyzed by reverse phase HPLC alone. By this method, PEG is separated not only from glyceride ethoxylates, but also from otherhydrophilic interferences that prevent analysis by reverse phase HPLC.

Analysis time for each sample is 90 minutes. Detection is by refractive index, and external standards are used for quantitation. The refractive index response is linear over a wide range of peg levels and varies very little with PEG molecular weight This method can be used to determine PEG levels as low as 0.04%.

As can be seen from the above, the process of the present invention provides a quick and easy way to produce a surfactant composition comprised of soap and moisturizing agents from a single reaction involving the saponification of certain alkoxylated triglycerides.

The foregoing description and examples illustrate selected embodiments of the present invention. In light thereof, variations and modifications will be suggested to one skilled in the art, all of which are in the spirit and purview of this invention.

What is claimed is:

1. A process for producing a surfactant composition comprising reacting an alkoxylated triglyceride having the formula:

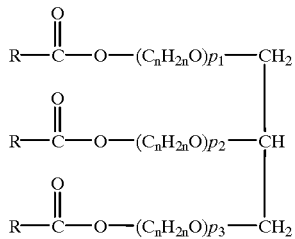

[I]

wherein n is from 2 to 4, $p_1$, $p_2$, and $p_3$ are each from about 1 to about 50, and R is an organic radical containing from about 1 to about 30 carbon atoms, with an alkali metal hydroxide, the mol ratio of alkoxylated triglyceride to alkali metal hydroxide being from 1:1 to 1:2.5, and recovering a surfactant composition comprising a soap having the general formula:

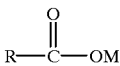

[II]

wherein M is an alkali metal, and a mixture of unreacted alkoxylated triglyceride, alkoxylated diglyceride, and alkoxylated monoglyceride.

2. The process of claim 1 wherein the mol ratio of alkoxylated triglyceride to alkali metal hydroxide is 1:1 to 1:2.

3. The process of claim 1 wherein the alkali metal hydroxide is sodium hydroxide.

4. The process of claim 1 wherein n is 2.

5. The process of claim 1 wherein R contains from 6 to 30 carbon atoms.

6. The process of claim 5 wherein R is a linear or branched-chain, saturated or unsaturated alkyl group.

7. The process of claim 1 wherein $p_1$, $p_2$, and $p_3$ are each from about 4 to about 20.

8. The process of claim 1 wherein the alkoxylated triglyceride is formed from a triglyceride derived from a natural source.

9. The process of claim 1 wherein R is a linear or branched chain alkyl group.

* * * * *